United States Patent [19]

Estabrook et al.

[11] Patent Number: 5,346,502

[45] Date of Patent: Sep. 13, 1994

[54] LAPAROSCOPIC ULTRASONIC SURGICAL INSTRUMENT AND METHODS FOR MANUFACTURING THE INSTRUMENTS

[75] Inventors: Brian K. Estabrook, Foxboro; Stephen DiMatteo, Seekonk, both of Mass.; Lionel J. Motta, Coventry, R.I.; John C. Wright, Mystic, Conn.

[73] Assignee: Ultracision, Inc., Smithfield, R.I.

[21] Appl. No.: 46,852

[22] Filed: Apr. 15, 1993

[51] Int. Cl.$^5$ .............................................. A61B 17/32
[52] U.S. Cl. ................................... 606/169; 76/104.1; 76/119; 601/2
[58] Field of Search ....................... 606/169, 167, 185; 128/24 AA; 30/340, 342; 76/119, 104.1, 106

[56] References Cited

U.S. PATENT DOCUMENTS

| | | | |
|---|---|---|---|
| 2,668,529 | 2/1954 | Huter | 128/24 AA |
| 3,630,192 | 12/1971 | Jamshidi | 128/754 |
| 3,990,452 | 11/1976 | Murry et al. | 606/169 |
| 5,026,387 | 6/1991 | Thomas | 606/169 |
| 5,047,043 | 9/1991 | Kubota et al. | 606/169 |
| 5,059,210 | 10/1991 | Clark et al. | 606/169 |
| 5,123,903 | 6/1992 | Quaid et al. | 606/169 X |
| 5,242,385 | 9/1993 | Strukel | 606/169 X |
| 5,263,937 | 11/1993 | Shipp | 606/167 X |

*Primary Examiner*—Michael H. Thaler
*Attorney, Agent, or Firm*—Nixon & Vanderhye

[57] ABSTRACT

The ultrasonic instrument includes a shaft having an integral sheath of PTFE encompassing the shaft and attached solely to the shaft. At the proximal end of the shaft, wrench flats are exposed through openings in the sheath and grooves cooperate with complementary ribs on the sheath, to prevent relative longitudinal and rotational displacement of the sheath and shaft. The sheath is in contact with the shaft at the nodes along the shaft. The diameter of the sheath is about 5 mm whereby the instrument may be used with a 5 mm trocar port. To manufacture the instrument, the sheath is initially formed to a diameter equal to or less than the diameter of the shaft and then mechanically expanded. Subsequently, the sheath is heat-shrunk about the shaft and rolled continuously along the shaft, except at regions corresponding to the nodes along the shaft, to expand the sheath to a larger diameter to space the sheath from the shaft except at the nodes of the shaft.

41 Claims, 6 Drawing Sheets

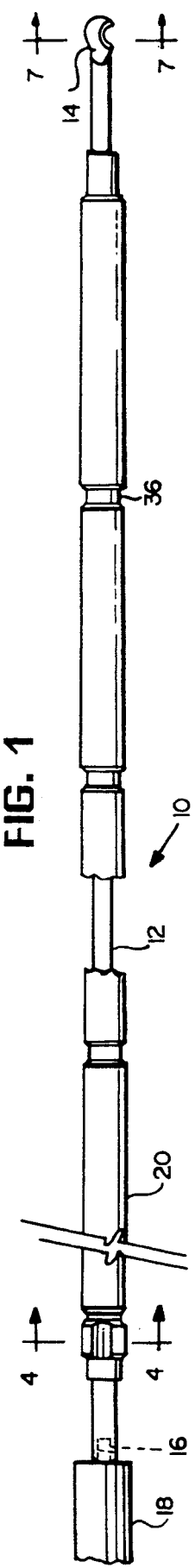
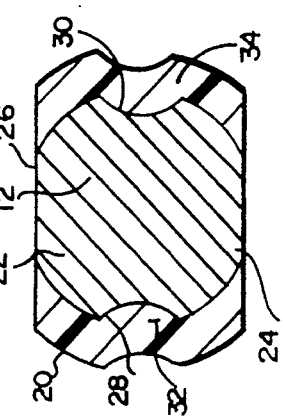
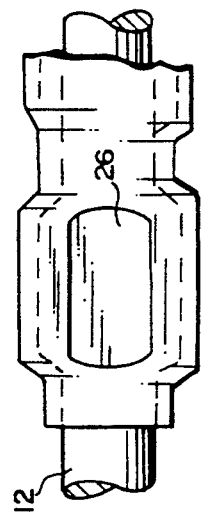
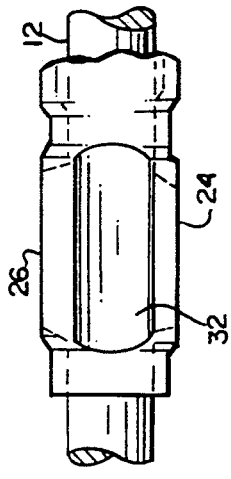

LAPAROSCOPIC ULTRASONIC SURGICAL INSTRUMENT AND METHODS FOR MANUFACTURING THE INSTRUMENTS

TECHNICAL FIELD

The invention relates generally to ultrasonic surgical instruments for applying ultrasonic energy at surgical sites for tissue dissection and coagulation and particularly to an ultrasonic instrument having reduced diameter for laparoscopic use in the treatment of large tissue areas, while simultaneously enabling reduced incisions and smaller scars. This present invention also relates to methods for manufacturing the ultrasonic surgical instrument.

BACKGROUND

Use of ultrasonically vibrating surgical blades to cut and coagulate tissue has previously been disclosed, for example, in U.S. Pat. No. 2,714,890. The benefits of using ultrasonic energy for tissue dissection and coagulation are many, e.g., enhanced cutting speed, simultaneous hemostasis and cutting, freedom from electrical hazards since no electrical current flows in the tissue, elimination of smoke and reduced build-up of eschar and other material on the blade. An ultrasonic surgical instrument adapted for laparoscopic usage under endoscopic observation has been described in prior U.S. patent application Ser. Nos. 07/670,186, filed Mar. 15, 1991, now abandoned and 07/828,697, filed Feb. 3, 1992, now abandoned, disclosures of which are incorporated herein by reference. From a review of those disclosures, it will be appreciated that there is an evolving use of ultrasonic instruments for laparoscopic surgery. In those instruments, a shaft diameter of approximately 10 mm or more was believed necessary for a number of reasons: (1) the ultrasonic energy transmission waveguide, i.e., a shaft, should have a sufficiently large diameter to provide the necessary strength to carry the desired ultrasonic energy without failure from fatigue; (2) there should be sufficient space for a protective sheath which surrounds the waveguide, i.e., the shaft, to prevent coupling of the ultrasonic energy to tissue or devices adjacent to it; and (3) the shaft should have a sufficiently large diameter to obtain the desired stiffness to allow the surgeon to supply side, as well as longitudinal, forces to the tissue.

While the ultrasonic laparoscopic instruments disclosed in the above-identified prior applications, of common assignee herewith, are eminently suitable for their intended purposes, there is the limitation that they require use of a 10 mm diameter trocar port which, in turn, creates a larger incision and scar than would be the case when using smaller available ports. Because most laparoscopic procedures involve the use of both 5 and 10 mm trocar ports, a 5 mm diameter device for laparoscopic surgery would enable the surgeon to choose from a greater variety of approaches to the surgical site because a 5 mm device can be used through either a 5 or 10 mm trocar port. There are, however, difficulties in reducing the diameter of an ultrasonic laparoscopic instrument for use with a 5 mm trocar port consistent with the above-identified criteria for effectively transmitting ultrasonic energy to the blade to enable dissection and coagulation. For example, in most prior ultrasonic devices which employ a sheath, it is required that the sheath be telescoped over the shaft from one end. Consequently, the sheath must have a larger diameter than the outside diameter of the shaft and at least one of the blade and shaft coupling at its proximal end to the handpiece. Where the sheath inner diameter is smaller than the outside diameter of both the blade and the shaft coupling to the ultrasonic transducer, the acoustic drive train, i.e., the shaft, must be formed into separable pieces to enable the user to remove the sheath. In this connection, see U.S. Pat. No. 3,861,391.

DISCLOSURE OF THE INVENTION

According to the present invention, there is provided an ultrasonic surgical instrument adapted for laparoscopic use for tissue dissection and coagulation and which is compatible for use with 5 mm trocar ports, while retaining the performance and sheathing protection of larger diameter instruments of this type. Thus, large diameter active blades for treatment of large tissue areas and a larger diameter proximal end enabling the formation of a strong joint between the handpiece and the shaft may be used, while simultaneously the instrument may be used with a smaller trocar port with its benefit of a smaller incision and scar. Additionally, the present invention enables the manufacture of and provides an ultrasonic instrument comprised of a large diameter ultrasonic blade at the distal end of the shaft, a large diameter proximal shaft end and a smaller diameter ultrasonically vibrating shaft therebetween, together with an ultrasonically inactive sheath having a small overall outside diameter and which sheath is strong, durable and readily manufactured. By providing a finally assembled instrument wherein the sheath cannot be removed from the blade, shaft and coupling combination, a one-piece instrument is provided enabling the user to conveniently exchange instruments, e.g., with respect to a handpiece, during an operation or between operations. Additionally, the manufacturing process hereof enables the use of an integral blade, shaft and coupling for the ultrasonic handpiece, hence enabling use of a one-piece blade, shaft and coupling combination, which is less expensive and stronger than two or three pieces forming that combination and is preferably formed of titanium. Discrete spacers between the blade and sheath, which are difficult to locate during manufacturing, are avoided, while blade support at the vibratory nodes along the shaft is maintained.

To accomplish the foregoing, the present invention provides a surgical instrument including an integral titanium blade, shaft and proximal end coupling for attaching the shaft to the handpiece which contains a piezeoceramic transducer. As will be appreciated, the piezeoceramic transducer is driven by an electrical signal from an ultrasonic generator and ultrasonic energy is thus transmitted along the shaft to the blade during use. The sheath encompassing the shaft is connected solely to the shaft and not directly to the handpiece. By this arrangement, unwanted vibrations, for example, those transverse to the shaft axis are reduced. Dissipation of the desired ultrasonic energy transmitted from the handpiece along the shaft to the blade is also minimized. More particularly, the proximal end of the shaft has a female threaded axial bore for connection to a threaded male stud on the handpiece for transmitting ultrasonic energy from the handpiece to the shaft. Forwardly along the shaft from this coupling and forming part of the proximal shaft end, there is provided a pair of diametrically opposed flats along a diametrically enlarged portion. A sheath encompasses the shaft and the enlarged diameter end portion of the shaft. The sheath has a pair of openings for exposing the flats externally of the sheath whereby a wrench may be applied to the flats to facilitate threaded application of the shaft to the handpiece. The margins of the openings through the sheath and the flats prevent relative longitudinal displacement of the shaft and sheath. The enlarged diameter proximal portion of the shaft is also grooved on its opposite sides and complementary inwardly directed projections formed on the sheath engage in the grooves to prevent relative rotation between the sheath and shaft.

At the opposite end of the sheath, and at a reduced diameter portion of the shaft, there is provided a sealing ring whereby the sheath is supported in spaced relation to the shaft at a node. The sheath, however, is in contact with the shaft at one or more of the vibratory nodes along the shaft. Thus, all contact between the sheath and shaft is substantially at the vibratory nodes and this minimizes dissipation of desired ultrasonic energy transmitted from the handpiece along the shaft to the blade, while simultaneously dissipating unwanted vibrations, e.g., transverse vibrations, to the sheath.

Preferably and importantly, the sheath is formed integrally of a polymeric material such as PTFE. There is substantial benefit in forming an integral sheath from a polymeric material in the resulting apparatus, as well as in its manufacture. For example, contact between the blade and sheath is at fundamental vibration nodes which does not significantly dampen the desired ultrasonic vibration because the longitudinal amplitude is small at those nodes. Unwanted vibrations occur at other frequencies and in modes which do not share the same nodal points as the desired mode. Thus, unwanted vibrations couple energy into the sheath and, because the polymeric material of the sheath is not an efficient conductor of vibration, the unwanted vibrational energy is quickly dissipated as heat. Unwanted vibration modes are therefore damped out by the sheath contact. As discussed herein, PTFE has a shape memory characteristic which is utilized during manufacture of the instrument.

To manufacture the ultrasonic instrument of the present invention, with the sheath having a diameter of about 5 mm, yet affording the necessary dissecting and coagulating functions of the instrument, the sheath is first extruded or molded into a tube form with an inside diameter smaller than the desired final diameter. The tube is then expanded, preferably mechanically at ambient temperature, so that its inside diameter is greater than the maximum diameter of the blade and the enlarged diameter portion at the proximal end of the shaft. Because of the mechanical expansion of the originally extruding PTFE material, the expanded sheath will remember its original extruded diameter. The shaft is then inserted within the sheath. The shaft and sheath are then heated, e.g., to approximately 625°-650° F., to cause the sheath to shrink toward its remembered original diameter such that the inside diameter of the sheath is less than the maximum diameter of the blade and proximal end. Preferably, the sheath is shrunk into contact with the shaft between the proximal shaft end and the blade. The portions of the sheath overlying the blade and the proximal end of the shaft are then removed, as well as the portions overlying the wrench flats. The sheath is then expanded away from the blade, except at the vibration nodes, the distal end sealing ring and the wrench flats. To accomplish this, the wall thickness of the sheath is reduced, for example, by pressing it between two rigid surfaces, while preventing the sheath from being longitudinally stretched. This enables the sheath to expand its diameter. Particularly, and in a preferred embodiment, the sheath is rolled between the shaft and a hard arcuate concave surface, except at the nodes, to expand the sheath, away from the shaft. This leaves the sheath material at the nodes in contact with the shaft. Alternatively, for short sheaths, the sheath can be rolled to enlarge its diameter relative to the shaft over its entire length and left that way, with the attachment between the shaft and sheath remaining at the enlarged wrench flats area at the proximal end of the shaft and the bearing ring at the distal end. As a further alternative, the entirety of the sheath can be enlarged relative to the shaft, as indicated, and subsequently, the sheath can be crimped or heat-shrunk at axial locations corresponding to the vibration nodes of the shaft to effect contact between the sheath and shaft and consequent mutual support therebetween.

An alternative manufacturing process provides a polymeric tube with an inside diameter corresponding to the diameter of the final sheath. Pressure and high temperature, e.g., 650°-800° F., are applied only to axial locations therealong corresponding to the nodal regions of the shaft to reduce their diameter to slightly less than the outside diameter of the shaft. The tube is then expanded, preferably mechanically, so that its inside diameter is greater than the diameter of the blade and enlarged proximal end of the shaft. The tube is then slipped over the blade and shaft and the temperature raised to cause the tube to shrink. When the reduced diameters at the nodal regions shrink into contact with the blade shaft, the balance of the sheath reaches its minimum inner diameter but remains out of contact with the shaft.

In a preferred embodiment according to the present invention, there is provided ultrasonic surgical apparatus comprising an elongated shaft having a proximal end and a surgical blade at a distal end, the proximal end, the shaft and the blade being integrally formed with one another and adapted to transmit ultrasonic energy therealong from the proximal end to the blade and a sheath extending about and generally radially spaced from the shaft, the largest lateral dimensions of the proximal end and the blade being greater than the internal diameter of the sheath.

In a further preferred embodiment according to the present invention, there is provided ultrasonic surgical apparatus comprising a surgical blade, a shaft carrying the blade at a distal end thereof and adapted at its proximal end for connection to a power element for generating ultrasonic energy and transmitting the ultrasonic energy along the shaft to the blade, a sheath extending about and generally radially spaced from the shaft and means between the sheath and the shaft isolating the ultrasonic energy transmitted along the shaft to the blade from the sheath. Means are carried by the shaft for cooperating with a tool to enable securement of the shaft with the sheath extending about the shaft to the power element.

In a still further preferred embodiment according to the present invention, there is provided ultrasonic surgical apparatus comprising a surgical blade, a shaft carrying the blade at a distal end thereof and adapted at its proximal end for connection to a power element for generating ultrasonic energy and transmitting the ultrasonic energy along the shaft to the blade, a sheath extending about and generally radially spaced from the shaft and means integral to one of the sheath and the shaft and engaging another of the sheath and the shaft for isolating the ultrasonic energy transmitted along the shaft to the blade from the sheath. Means are provided cooperable between the shaft and the sheath for precluding substantial rotational movement of the shaft and sheath relative to one another.

In a still further preferred embodiment according to the present invention, there is provided a method of manufacturing an ultrasonic surgical apparatus including a shaft for connection at one end to a power element for the transmission of ultrasonic energy along the shaft to a surgical blade at its opposite end and a sheath substantially encompassing the shaft and in contact therewith at predetermined locations along the shaft, comprising the steps of forming the sheath to a diameter in excess of the diameter of the shaft, relatively locating the sheath and shaft such that the shaft lies within the sheath, decreasing the diameter of the sheath into contact with the shaft and applying pressure to the sheath at least one location along its length to diametrically enlarge the sheath and space the sheath from the shaft at the one location.

In a still further preferred embodiment according to the present invention, there is provided a method of manufacturing an ultrasonic surgical apparatus including a shaft for connection at one end to a power element for the transmission of ultrasonic energy along the shaft to a surgical blade at its opposite end and a sheath substantially encompassing the shaft and in contact therewith at the vibratory nodes along the shaft, comprising the steps of forming the sheath to a diameter in excess of the diameter of the shaft, applying heat and pressure to the sheath along its length, at least one predetermined location to diametrically decrease the sheath at the one location to a diameter less than or equal to the diameter of the shaft, enlarging the diameter of the sheath so that the inside diameter of the sheath is larger than the maximum diameter of the shaft, relatively locating the sheath and shaft such that the shaft lies within the sheath and heat shrinking the sheath to decrease the diameter of the sheath to bring the one diametrically decreased location along the sheath into contact with the shaft, leaving remaining portions of the sheath spaced from the shaft.

In a still further preferred embodiment according to the present invention, there is provided a method of manufacturing an ultrasonic surgical apparatus including a shaft for connection at one end to a power element for the transmission of ultrasonic energy along the shaft to a surgical blade at its opposite end and a sheath substantially encompassing the shaft and in contact therewith at one or more radial projections along the shaft at vibratory nodes thereof, comprising the steps of forming the sheath to a diameter approximately equal to or less than the diameter of the shaft, applying a solvent to the sheath to diametrically increase the diameter of the sheath so that the inside diameter of the sheath is larger than the maximum diameter of the shaft, relatively locating the sheath and shaft such that the shaft lies within the sheath and removing the solvent from the sheath to decrease the diameter of the sheath to bring the sheath into contact with the radial projections of the shaft, leaving remaining portions of the sheath spaced from the shaft.

Accordingly, it is a primary object of the present invention to provide a novel and improved ultrasonic surgical instrument adapted for laparoscopic use, particularly for use with a 5 mm trocar port, and methods for manufacturing the instrument.

BRIEF DESCRIPTION OF THE DRAWINGS

FIG. 1 is a side elevational view with portions broken out of an ultrasonic surgical apparatus manufactured in accordance with the present invention illustrating its shaft, sheath, blade and a portion of a handpiece;

FIG. 2 is an enlarged side elevational view of the wrench flats region of the combined shaft and sheath of the instrument hereof;

FIG. 3 is a view similar to FIG. 2, with the instrument rotated 90° about its axis;

FIG. 4 is an enlarged cross-sectional view taken generally about on line 4—4 in FIG. 1;

BEST MODE FOR CARRYING OUT THE INVENTION

Figure 5:
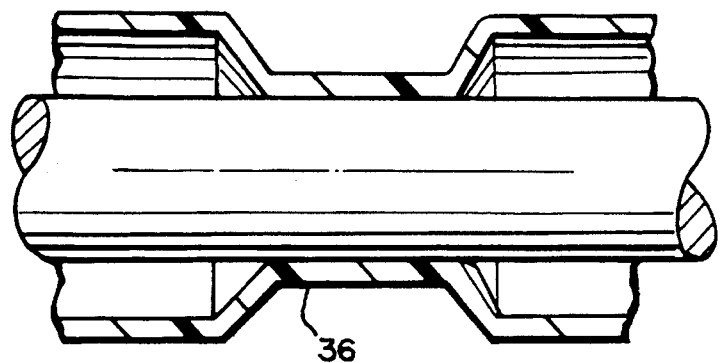
FIG. 5 is an enlarged cross-sectional view of the sheath in contact with the shaft at a vibratory node.
Figure 6:
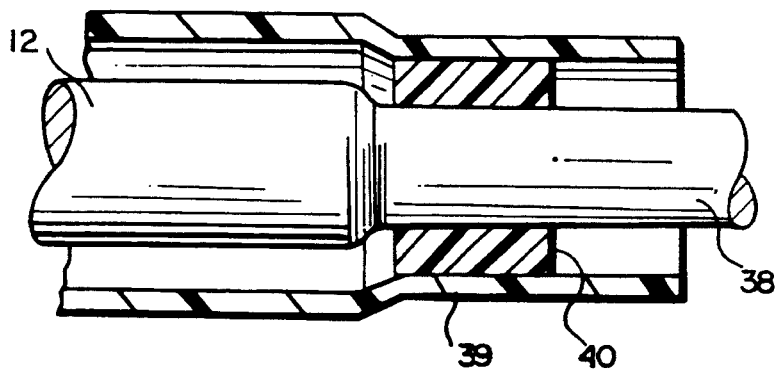
FIG. 6 is a view similar to FIG. 5 illustrating the contact between the sheath and shaft adjacent the blade end of the instrument.

Referring now to the drawings, particularly to FIG. 1, there is illustrated a surgical instrument, generally designated 10, constructed in accordance with the present invention, and comprised of a shaft 12 having a blade 14 at its distal end and a female threaded bore 16 at its proximal end for threaded connection with a threaded male stud projecting from a handpiece 18. Surrounding shaft 12 and connected solely to the shaft is a sheath 20 formed integrally of a polymeric material for reasons discussed below. It will be appreciated that handpiece 18 contains a piezeoceramic transducer driven by an electrical signal from an ultrasonic generator for transmitting ultrasonic energy to the shaft through the threaded connection with the shaft to provide longitudinal vibratory movement at blade 14. Thus, in use, the ultrasonic energy is supplied from the handpiece at, for example, a frequency of 55,500 Hz, for transmission along the shaft to blade 14.

Shaft 12 is preferably formed of titanium and is formed integrally throughout its extent, including blade 14 at its distal end and the female bore 16 at its proximal end. Spaced from bore 16 and at the proximal end is an enlarged diameter portion 22 of shaft 12 in which there is provided flats 24 and 26 on opposite sides of the shaft, preferably at a node. Between flats 24 and 26 and spaced 90° therefrom are radially inwardly projecting grooves 28 and 30. Sheath 20 at its proximal end overlies shaft 12 and has opposite sides cut away to expose flats 24 and 26 externally of sheath 20. Along the sides of the sheath 20, there are provided radially inwardly projecting ribs 32 and 34 for engaging the complementary-shaped grooves 28 and 30 on shaft 12. In the final product, the engagement of the ribs and grooves prevents relative rotation of the shaft and sheath, while the margins of the openings of the sheath about flats 24 and 26 prevent relative longitudinal movement between the sheath and the shaft. The engagement of the sheath and shaft at the enlarged diameter portion 22 of the shaft is at a vibratory node along the shaft. Sheath 20 has longitudinally spaced, radially inwardly directed portions 36 engaging the shaft at other vibratory nodal locations along the shaft, for example, as illustrated in FIG. 5. At the distal end of sheath 20, a sealing ring 40 is provided between a reduced diameter portion 38 of shaft 12 and similarly reduced diameter portion 39 of the sheath and preferably at a vibratory node of the shaft. Ring 40 is formed of a compliant material, preferably silicone. Ring 40, in conjunction with the portions 36 of sheath 20 which engage shaft 12, as well as the proximal end of the sheath engaging the flats and grooves of the shaft, minimize dissipation of desired ultrasonic energy at the contact points between the shaft and sheath, while affording dissipation of unwanted vibrational energy of different modes, for example, transverse vibrational energy, into sheath 20. Sealing ring 40 also prevents passage of gas or fluid between the sheath and shaft.

Figure 7:
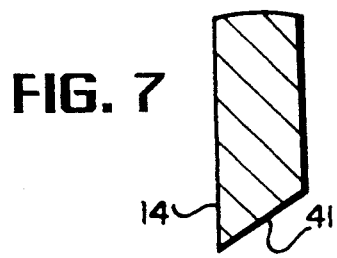
FIG. 7 is a cross-sectional view of the blade taken generally about on line 7—7 in FIG. 1.

It will be appreciated that the diameter of the sheath is about 5 mm and that the diameters of the blade 14 and enlarged diameter proximal portion of the shaft may be larger than 5 mm. The blade diameter can also be 5 mm or less. By maintaining the diameter of the sheath about 5 mm and providing a blade diameter of 5 mm or less, the surgical instrument hereof may be used with a 5 mm trocar port. It will also be appreciated that any number of different types of blades may be used and formed integrally with the shaft. An example of a hook-type blade 14 is illustrated and which blade has a tapered arcuate cutting edge 41 as illustrated in FIG. 7.

Figure 8:
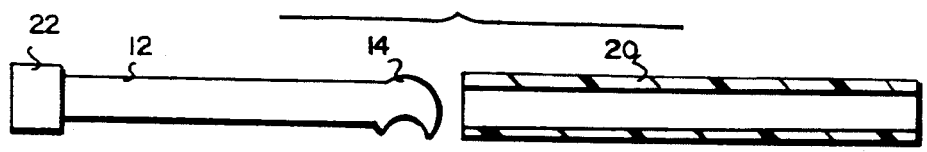
FIGS. 8a–8f are schematic illustrations of a method of manufacturing the instrument, particularly a method of applying the sheath to the shaft to achieve a diameter of 5 mm or less.
Figure 8A:
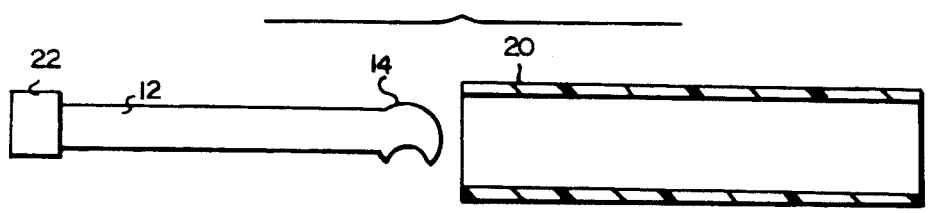
Figure 8B:
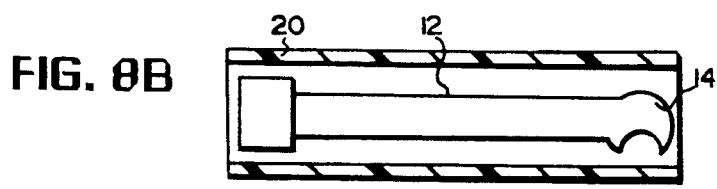
Figure 8C:
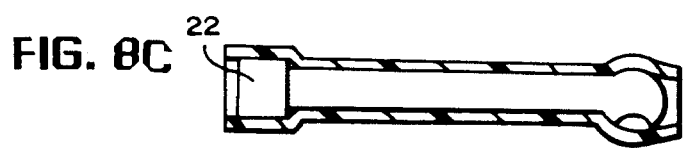
Figure 8D:
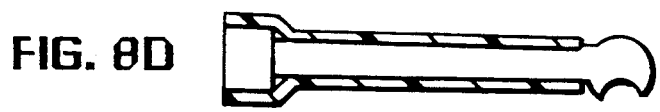

In order to form the instrument hereof with the sheath diameter reduced to about 5 mm, reference is made to FIG. 8. In the schematic illustration of FIG. 8, shaft 12 has an integral enlarged diameter portion 22 at its proximal end and an integral enlarged diameter portion at its distal end constituting blade 14. Also illustrated is a molded or extruded tube which will eventually form the sheath 20. As illustrated, tube 20 has an inside diameter initially smaller than the desired diameter of the sheath in the final product. The sheath has also been molded or extruded at high temperatures, for PTFE about 700°-800° F., and then cooled to ambient temperature whereby the material will remember its initially formed diameter. With reference to FIG. 8A, tube 20 has been diametrically expanded, preferably mechanically, e.g., pulled over a mandrel or by air pressure, so that the inside diameter of tube 20 is greater than the maximum diameter of the enlarged portion 22 and blade 14. In FIG. 8B, it will be seen that the tube 20 and shaft 12 have been telescoped relative to one another such that shaft 12, portion 22 and blade 14 lie within the tube 20. Heat is now applied to the sheath and shaft illustrated in FIG. 8B to cause tube 20 to shrink about shaft 12, blade 14 and enlarged portion 22, as illustrated in FIG. 8C. For example, an oven may be used to heat the assembly or, alternatively, hot air from a heat gun may be used. Because the tube has been formed by an initial extrusion or molding to a certain diameter, once enlarged and in response to the application of heat, the tube will shrink toward its remembered original diameter. Full recovery of its initial diameter is temperature dependent and, for PTFE, temperatures on the order of 625°-650° F. will enable the sheath to shrink to its initial remembered diameter. Once the tube has been shrunk into contact with shaft 12, the excess portions of the sheath may be removed. For example, the portions of the sheath about blade 14, as well as the portions overlying the flats of the shaft, may be removed from the assembly as illustrated in FIG. 8D.

Figure 8E:
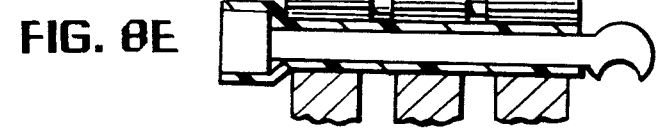
Figure 8F:
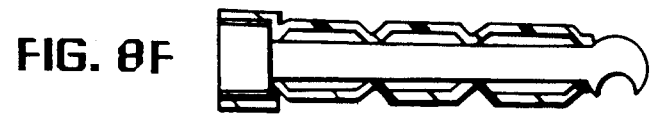

With respect to FIG. 8E, the tube 20 is expanded away from the outer surface of shaft 12 in the areas of the tube surrounding shaft 12, excluding the enlarged portion 22 and locations corresponding to the nodal regions of the shaft. By pressing the wall of the sheath between two rigid members, while preventing longitudinal stretching of the tube, the tube will expand in diameter. While two planar surfaces may be used and between which the sheath and shaft may be rolled, rollers 42 are preferable. Rollers 42 roll tube 20 against the shaft 12 to expand the diameter of the tube. Preferably, the rolling action is provided throughout the length of the sheath, except for portions overlying the proximal end portion and at locations corresponding to the vibratory nodes of the shaft. Consequently, the sheath will expand to a larger diameter by thinning the material only in those areas spaced longitudinally from the vibratory nodes, leaving the portions of the sheath between the rollers in contact with the shaft, i.e., leaving portions 36, one of which is illustrated in FIG. 5, in contact with shaft 12. Thus, sheath 20 is spaced from the surface of shaft 12 throughout substantially its entire length, except for the contact made at the vibratory nodes.

Figure 9:
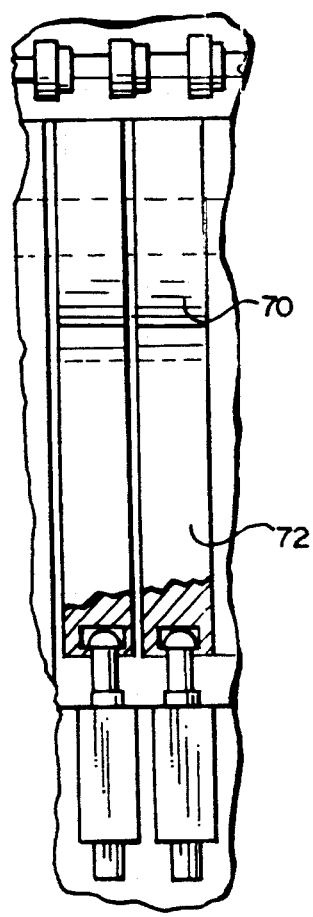
FIG. 9 is a fragmentary plan view illustrating a preferred form of manufacturing the instrument.
Figure 10:
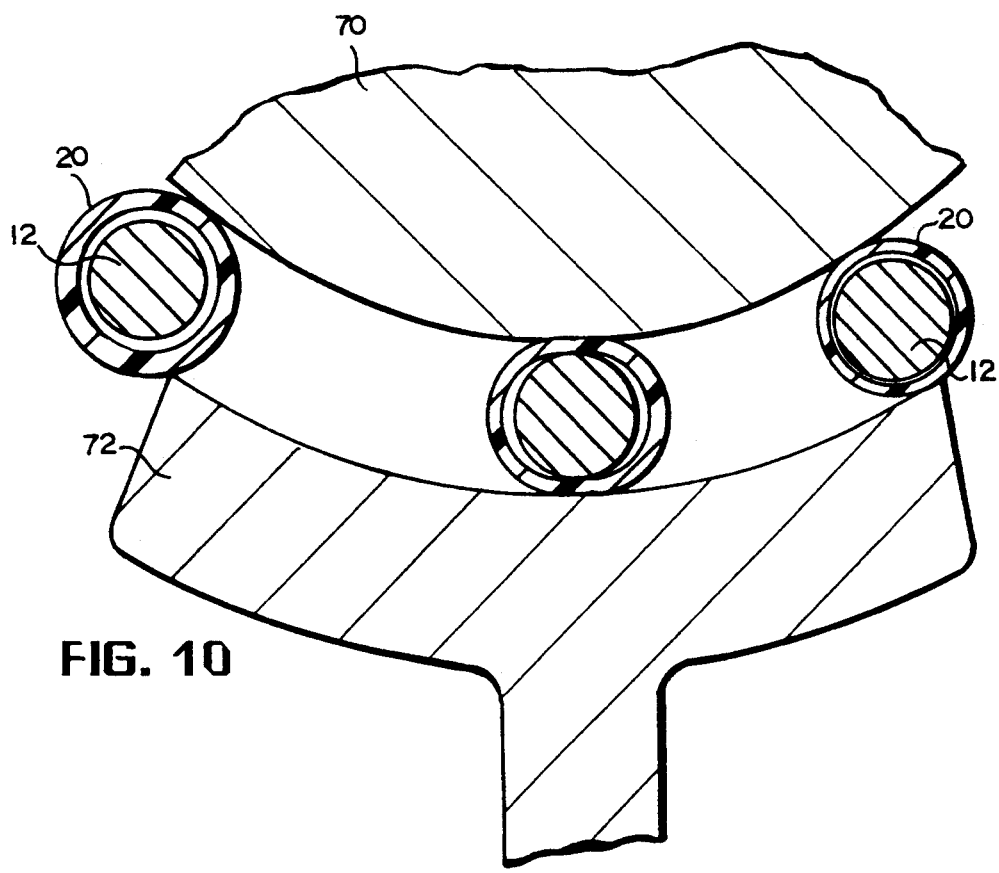
FIG. 10 is an enlarged cross-sectional view illustrating the manner in which the sheath is enlarged relative to the shaft.
Figure 11A:
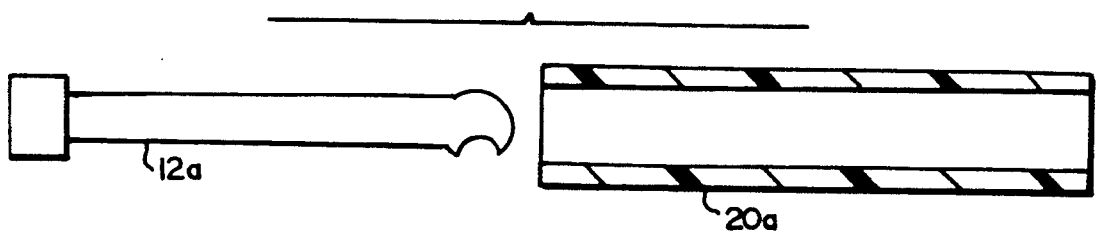
FIGS. 11a–11f are schematic illustrations of an alternative method of manufacturing the instrument.
Figure 11B:
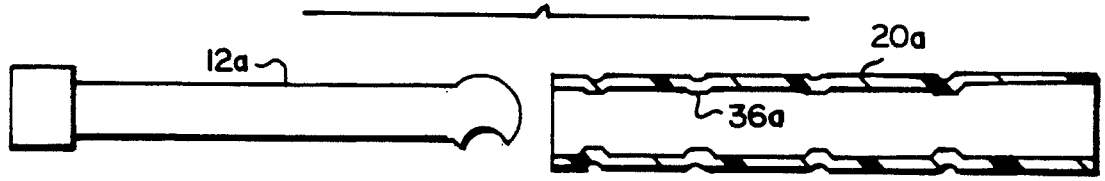
Figure 11C:
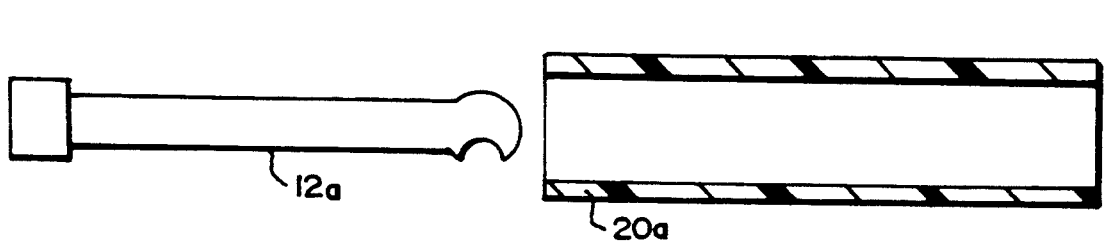
Figure 11D:
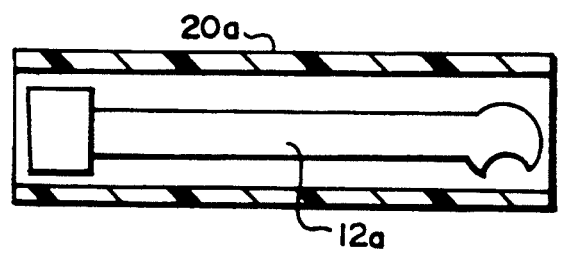
Figure 11E:
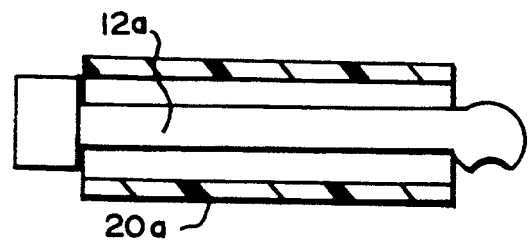
Figure 11F:
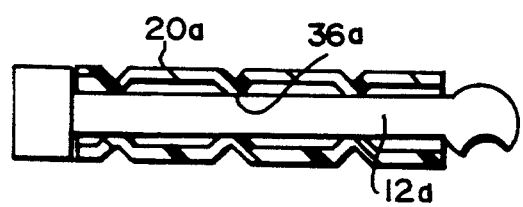

More particularly, and referring to FIGS. 9 and 10, the shaft and sheath are placed between rollers 70 and a series of large diameter concave surfaces 72 diametrically opposed to the rollers and biased for movement, e.g., by an air cylinder, toward the rollers 70. Each concave surface backs the sheath and shaft when pressure is applied to thin the polymeric material along the lines of contact and hence to enlarge the diameter of the sheath. The line contacts between the rollers and sheath and between the sheath and the concave surfaces on diametrically opposite sides prevent longitudinal expansion of the polymeric material necessitating diametrical enlargement of the sheath due to thinning of the polymeric material of the sheath. A rolling action in one direction, between the rollers and the concave surface thus expands the sheath only at axial locations where the polymeric material is thinned and not at axial locations where it is not thinned, i.e., at axial locations corresponding to the nodes of the shaft. While the sheath may obtain a slight oval cross-section during rolling, that cross-section becomes a circular cross-section upon removal of the sheath and shaft from between the rollers and concave surfaces. Also, a back-and-forth rolling action between the rollers and concave surfaces obtains similar results.

Alternatively, the rollers 42 can press the sheath against the shaft to enlarge the entire diameter of the sheath, excluding the portion of the sheath about the enlarged portion 22. Localized crimping or heat-shrinking of the sheath at the vibratory nodes can subsequently be effected to bring the portions 36 into contact with the shaft surface at the vibratory nodes. Once the sheath has been expanded and the portions 36 contact the vibratory nodes, further excess material of the sheath may be removed from one or both ends of the sheath to achieve the desired sheath length. Additionally, the material of the sheath may be removed to expose the wrench flats.

A slight variation of the foregoing process may also be used. For example, as illustrated in FIGS. 11a–11f, the sheath 20a may be extruded or formed into a tube with the inside diameter in excess of the diameter of the final product as in FIG. 11a. Elevated temperatures, e.g., 700°–750° F. (original processing temperatures), and elevated pressure may be applied to the regions of the sheath corresponding to the nodes along the shaft to reduce the diameter of the tube at those regions 36a to a diameter less than or equal to the outside diameter of the shaft. Thereafter, the sheath 20a can be mechanically expanded, e.g., over a mandrel, so that the sheath inside diameter is smooth bored and is greater than the maximum diameter of the blade and the enlarged proximal end portion of the shaft. When the shaft 129 is received within the sheath, as in FIG. 11d, heat, e.g., 625°–650° F., may be applied to the sheath to cause the tube to shrink and return to its remembered configuration with the original diameter and the reduced diameter regions 36a. The reduced diameter regions of the sheath will shrink with the sheath and contact the shaft, leaving the rest of the sheath spaced from the shaft. Thus, the rolling step alluded to in the previously described method may be avoided. As in the prior embodiment, the extra length of the sheath and the material along the wrench flats may be removed.

It will be appreciated that, in accordance with the present invention, the instrument comprising the integral shaft, proximal end and blade together with the sheath extending about the shaft may be applied to a power generating element, e.g., handpiece 18, by the threaded connection previously described. To accomplish this, a wrench may be applied to the flats 26 exposed through the apertures through the sheath. In alternative forms, the sheath may terminate short of the flats 26 or the flats may be engaged by the wrench with the sheath overlying the flats. In any of these alternatives, the combined shaft, proximal end, blade and sheath are desirably and beneficially applied to and removed from the power generating element as a unit.

Figure 12:
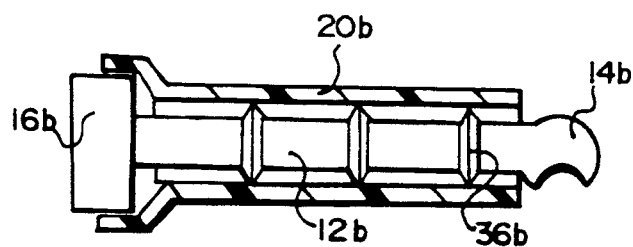

Referring now to FIG. 12, there is illustrated a further form of laparoscopic instrument according to the present invention wherein the blade shaft 12b has radial projections or regions 36b located at the nodes of the shaft. Sheath 20b, formed of a polymeric material such as PTFE, encompasses shaft 12b in contact with the radial projections 36b but is otherwise spaced from the shaft 12b. Consequently, the sheath 20b is isolated from the ultrasonic energy transmitted along shaft 12b by the radial projections or regions 36b located at the nodes along the shaft and which projections 36b are integral with shaft 12b. In this form of instrument, it will be appreciated that the outside diameters of projections 36b are equal to or greater than the largest diameter of the blade 14b or proximal end portion 16b. Preferably, the inside diameter of the sheath 20b is slightly smaller than the outside diameter of the projections 36b. This enables the sheath to be pulled over the shaft or the shaft inserted into the sheath with the sheath in contact with the shaft only at the projections 36b or at other node points, i.e., the proximal end portion 16b. The interference or frictional fits between the shaft projections 36b and the sheath 20b retain the sheath on the shaft.

If the blade tip diameter is larger than the outside diameter of the projections 36b, the polymeric tube may be extruded or molded initially with an inside diameter slightly smaller than the outside diameter of the regions 36b. The sheath may then be expanded mechanically to a larger outside diameter, slipped over the shaft and then heated, e.g., to about 600°–650° F., such that the tube shrinks to its remembered initial outside diameter and into contact with the regions 36b. When contact is made, the heat is removed such that the portions of the sheath between its contact with the regions 36b remain spaced from the shaft 12b.

Alternatively, the sheath 20b can be initially extruded or molded with a diameter just smaller than the outside diameter of the regions 36b. The sheath 20b may then be heated to about 600°–650° F. to cause the PTFE tube to thermally expand. The shaft and blade 12b and 14b, respectively, may then be inserted into the tube while the tube remains in its thermally expanded condition. Once the sheath and shaft are telescoped, the sheath is cooled to ambient temperature whereupon the material of the sheath contracts toward its original shape into contact with the regions 36b. The portions of the sheath between its contact with the regions 36b are spaced from the shaft 12b.

As a further alternative, the sheath may be chemically expanded from an original diameter just smaller than the outside diameter of the regions 36b. Thus, a polymer may be chosen which swells when it absorbs a solvent, e.g., a Freon solvent, will cause a silicone tube to swell. Once the tube has swelled to permit insertion of the shaft, the solvent is removed, whereupon the polymer sheath returns to its original shape and into contact with projections 36b with the remaining portions of the sheath spaced from the shaft.

Figure 13:
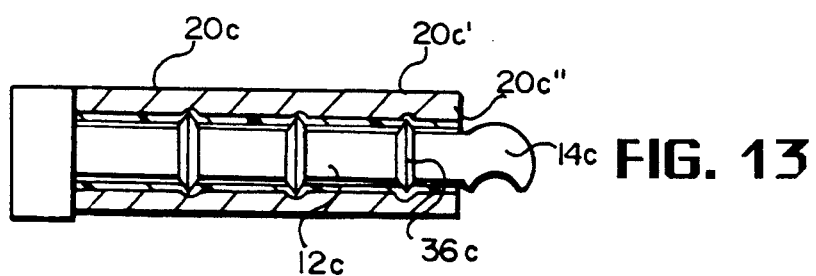
FIGS. 12–14 are longitudinal cross-sectional views illustrating further embodiments of the laparoscopic instrument of the present invention.

Referring to FIG. 13, there is illustrated another form of instrument having a shaft 12c with radially outward projections or regions 36c at the node points along the shaft. In this form, the sheath 20c comprises an outer layer of stainless steel 20c' and an inner layer of polymeric material 20c''. The sheath is dimensioned such that it can be slipped onto the shaft and retained thereon by an interference or friction fit with projections 36c in contact with the polymeric lining 20c''. The remaining portions of the lining between the regions 36c are spaced from the shaft. The relative dimensions of the sheath, shaft and blade tip 14c are similar to those of the embodiment hereof illustrated in FIG. 12. Consequently, in this embodiment, the inner layer is formed of a material of lower durometer than the durometer of the material of the outer layer.

Figure 14:
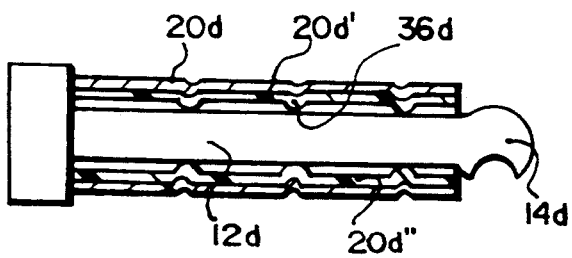

In FIG. 14, there is illustrated a further form of instrument, including an integral shaft 12d and an outer sheath 20d formed of a composite layer, for example, an outer layer of stainless steel 20d' and an inner layer 20'' of either a compliant material, such as silicone or a low coefficient of friction material, such as Teflon. In this form, the outside diameter of the blade 14d is equal to or smaller than the diameter of shaft 12d whereby the sheath 20d can be slipped on forming an interference fit with respect to the shaft 12d. The sheath 20d has preformed a plurality of projections 36d which contact the shaft 12d at the node points and maintain the balance of the sheath spaced from the shaft.

It will be appreciated that a combination of radial inward and radial outward projections on the sheath and shaft, respectively, may be employed at locations corresponding to the nodes of the shaft. For example, the flats on the shaft project outwardly and are located along the shaft at a node. A sheath having radial inward projections as illustrated in the embodiments of FIGS. 1–11 may be used with that shaft. Alternatively, radial outward projections may be employed at one or more of other nodes of the shaft in combination with a sheath which has one or more radially inward projections at a location(s) corresponding to the node(s) of the shaft. Also, instead of projections 36 integral with either the shaft or the sheath or both, discrete spacers, such as rings formed of silicone, may be located at the nodes.

While the invention has been described with respect to what is presently regarded as the most practical embodiments thereof, it will be understood by those of ordinary skill in the art that various alterations and modifications may be made which nevertheless remain within the scope of the invention as defined by the claims which follow.

What is claimed is:

1. Ultrasonic surgical apparatus comprising:
    an elongated shaft having a proximal end and a surgical blade at a distal end;
    said proximal end, said shaft and said blade being one-piece integral construction and adapted to transmit ultrasonic energy therealong from said proximal end to said blade; and
    a sheath extending about and generally radially spaced from said shaft;
    the largest lateral dimensions of said proximal end and said blade being greater than the smallest internal diameter of said sheath.

2. Apparatus according to claim 1 including means engaging between said shaft and said sheath for minimizing dissipation of the ultrasonic energy transmitted along said shaft.

3. Apparatus according to claim 1 including means directly cooperable between said sheath and said shaft for precluding substantial rotational movement of the sheath and shaft in opposite directions relative to one another.

4. Apparatus according to claim 1 wherein said sheath is formed of a polymeric material.

5. Apparatus according to claim 1 wherein said sheath is formed of polytetrafluoroethylene.

6. Apparatus according to claim 1 wherein said sheath comprises outer and inner layers, said inner layer being formed of a material having a lower durometer than the durometer of the material forming said outer layer.

7. Apparatus according to claim 1 wherein said sheath comprises an outer layer formed of a polymeric material and an inner layer formed of silicone.

8. Apparatus according to claim 1 wherein said sheath comprises outer and inner layers, said inner layer being formed of a material having a lower coefficient of friction than the coefficient of friction of the material forming said outer layer.

9. Apparatus according to claim 1 including means for precluding substantial longitudinal movement of the sheath and shaft relative to one another, said sheath being formed of a polymeric material and connected solely to said shaft.

10. Apparatus according to claim 1 including means directly cooperable between said shaft and said sheath for precluding substantial rotational movement of the sheath and shaft in opposite directions relative to one another, and means integral to said sheath and engaging said shaft for minimizing dissipation of the ultrasonic energy transmitted along said shaft.

11. Apparatus according to claim 1 wherein said sheath is formed of a polymeric material, means integral with said sheath projecting radially inwardly thereof and engaging said shaft for minimizing dissipation of the ultrasonic energy transmitted along said shaft.

12. Apparatus according to claim 1 wherein said sheath is formed of a polymeric material, means integral with said shaft projecting radially outwardly thereof and engaging said sheath for minimizing dissipation of the ultrasonic energy transmitted along said shaft.

13. Apparatus according to claim 1 wherein said sheath is formed of polymeric material, and means disposed between said sheath and said shaft for minimizing dissipation of the ultrasonic energy transmitted along said shaft.

14. Apparatus according to claim 1 including at least one tool engaging surface on said shaft and at least one aperture opening laterally through said sheath exposing said tool engaging surface for access externally of said sheath.

15. Apparatus according to claim 1 including a pair of flats formed on laterally opposite sides of said shaft to form wrench engaging surfaces, a pair of apertures opening through said sheath in registration with and exposing said flats through said sheath for access by a wrench externally of said sheath.

16. Apparatus according to claim 15 including means for precluding substantial longitudinal movement of the shaft and sheath relative to one another, said precluding means including said projecting flats and said apertures.

17. Apparatus according to claim 1 including means carried by said shaft for cooperation with a tool to enable securement of the shaft with the sheath extending about the shaft to a generator of ultrasonic energy.

18. Apparatus according to claim 1 including means for precluding substantial longitudinal movement of the sheath and shaft relative to one another, said sheath being formed of a polymeric material, said precluding means including projections on one of said sheath and said shaft and complementary openings in another of said sheath and said shaft, means for precluding substantial rotational movement of said sheath and said shaft relative to one another including a rib formed on one of said shaft and said sheath and a complementary-shaped groove formed on another of said shaft and said sheath.

19. Apparatus according to claim 17 including means engaging between said shaft and said sheath for minimizing dissipation of the ultrasonic energy transmitted along said shaft, said ultrasonic energy dissipation minimizing means including an integral portion of said sheath engaging said shaft at least one vibratory node along said shaft, said shaft including a pair of flats along said shaft, said sheath being connected solely to said shaft, said sheath being formed of polytetrafluoroethylene.

20. Apparatus according to claim 1 wherein the outer diameter of said sheath is no greater than about 5 mm.

21. Apparatus according to claim 1 wherein said sheath is connected solely to said shaft.

22. Apparatus according to claim 1 including connective structure carried by said proximal end of said shaft for connecting said shaft to an ultrasonic transducer.

23. Apparatus according to claim 1 wherein said sheath is formed of a one-piece integral construction.

24. Apparatus according to claim 1 wherein said sheath has opposite ends terminating short of the proximal and distal ends of said shaft.

25. A method of manufacturing an ultrasonic surgical apparatus including a shaft for connection at one end to a power element for the transmission of ultrasonic energy along the shaft to a surgical blade at its opposite end and a sheath substantially encompassing said shaft and in contact therewith at predetermined locations along said shaft, comprising the steps of:
forming the sheath to a diameter in excess of the diameter of the shaft;
relatively locating the sheath and shaft such that the shaft lies within the sheath;
decreasing the diameter of the sheath into contact with said shaft; and
applying pressure to said sheath at least one location along its length to diametrically enlarge the sheath and space the sheath from the shaft at said one location.

26. A method according to claim 25 including forming the sheath to an initial diameter equal to or less than the diameter of the shaft and subsequently forming the sheath to the diameter in excess of the diameter of the shaft.

27. A method according to claim 26 wherein the step of decreasing the diameter of the sheath includes heating the sheath to shrink the sheath toward its initial diameter.

28. A method according to claim 27 wherein the sheath, when formed to a diameter in excess of the diameter of the shaft, has a memory of the initial diameter, the step of heating the sheath causing the sheath to return toward its remembered diameter.

29. A method according to claim 25 wherein the step of applying pressure includes pressing the sheath between a pair of surfaces to thin the material of the sheath thereby enlarging the diameter of the sheath.

30. A method according to claim 25 wherein the step of applying pressure includes pressing the sheath and shaft between first and second surfaces while rolling the sheath and shaft between the surfaces.

31. A method according to claim 25 wherein the step of applying pressure includes pressing the sheath and shaft between a roller and an arcuate surface wherein the sheath is pressed between the roller and the shaft along one side of the sheath and between the shaft and the arcuate surface along a diametrically opposite side of said sheath.

32. A method of manufacturing an ultrasonic surgical apparatus including a shaft for connection at one end to a power element for the transmission of ultrasonic energy along the shaft to a surgical blade at its opposite end and a sheath substantially encompassing said shaft and in contact therewith at the vibratory nodes along said shaft, comprising the steps of:
forming the sheath to a diameter in excess of the diameter of the shaft;
applying heat and pressure to said sheath along its length, at least one predetermined location to diametrically decrease the sheath at said one location to a diameter less than or equal to the diameter of the shaft;
enlarging the diameter of the sheath so that the inside diameter of the sheath is larger than the maximum diameter of the shaft;
relatively locating the sheath and shaft such that the shaft lies within the sheath; and
heat shrinking the sheath to decrease the diameter of the sheath to bring said one diametrically decreased location along the sheath into contact with said shaft, leaving remaining portions of the sheath spaced from the shaft.

33. A method of manufacturing an ultrasonic surgical apparatus including a shaft for connection at one end to a power element for the transmission of ultrasonic energy along the shaft to a surgical blade at its opposite end and a sheath substantially encompassing said shaft and in contact therewith at one or more radial projections along the shaft at vibratory nodes thereof, comprising the steps of:
forming the sheath to a diameter approximately equal to or less than the diameter of the shaft;
applying a solvent to said sheath to diametrically increase the diameter of the sheath so that the inside diameter of the sheath is larger than the maximum diameter of the shaft;
relatively locating the sheath and shaft such that the shaft lies within the sheath; and
removing the solvent from the sheath to decrease the diameter of the sheath to bring said sheath into contact with said radial projections of said shaft, leaving remaining portions of the sheath spaced from the shaft.

34. Ultrasonic surgical apparatus comprising:
a surgical blade;
a shaft carrying said blade at a distal end thereof and adapted at its proximal end for connection to a power element for generating ultrasonic energy and transmitting the ultrasonic energy along said shaft to said blade;
a sheath extending about and generally radially spaced from said shaft;
means between said sheath and said shaft for isolating the ultrasonic energy transmitted along said shaft to said blade from said sheath;
means carried by said shaft for cooperation with a tool to enable securement of the shaft with the sheath extending about the shaft to the power element; and
said securement and enabling means including at least one tool engaging surface on said shaft and at least one aperture opening laterally through said sheath exposing said tool engaging surface for access externally of said sheath.

35. Apparatus according to claim 34 including means for precluding substantial longitudinal movement of the shaft and sheath relative to one another, said precluding means including said tool engaging surface and said one aperture.

36. Apparatus according to claim 34 including means for precluding substantial longitudinal movement of the sheath and shaft relative to one another, said sheath being formed of a polymeric material, said precluding means including projections on one of said sheath and said shaft and complementary openings in another of said sheath and said shaft, means for precluding substantial rotational movement of said sheath and said shaft relative to one another including a rib formed on one of said shaft and said sheath and a complementary-shaped groove formed on another of said shaft and said sheath.

37. Apparatus according to claim 34 wherein the outer diameter of said sheath is no greater than about 5 mm.

38. Ultrasonic surgical apparatus comprising:
a surgical blade;

a shaft carrying said blade at a distal end thereof and adapted at its proximal end for connection to a power element for generating ultrasonic energy and transmitting the ultrasonic energy along said shaft to said blade;

a sheath extending about and generally radially spaced from said shaft;

means between said sheath and said shaft for isolating the ultrasonic energy transmitted along said shaft to said blade from said sheath;

means carried by said shaft for cooperation with a tool to enable securement of the shaft with the sheath extending about the shaft to the power element; and said securement enabling means including a pair of flats formed on laterally opposite sides of said shaft to form wrench engaging surfaces, a pair of apertures opening through said sheath in registration with and exposing said flats through said sheath for access by a wrench externally of said instrument.

39. Ultrasonic surgical apparatus comprising:

a surgical blade;

a shaft carrying said blade at a distal end thereof and adapted at its proximal end for connection to a power element for generating ultrasonic energy and transmitting the ultrasonic energy along said shaft to said blade;

a sheath extending about and generally radially spaced from said shaft;

means for isolating the ultrasonic energy transmitted along said shaft to said blade from said sheath;

means directly cooperable between said shaft and said sheath for positively precluding substantial rotational movement of the shaft and sheath in opposite directions relative to one another; and at least one tool engaging surface on said shaft and at least one aperture opening laterally through said sheath, exposing said tool engaging surface for access externally of said sheath.

40. Ultrasonic surgical apparatus comprising:

a surgical blade;

a shaft carrying said blade at a distal end thereof and adapted at its proximal end for connection to a power element for generating ultrasonic energy and transmitting the ultrasonic energy along said shaft to said blade;

a sheath extending about and generally radially spaced from said shaft;

means for isolating the ultrasonic energy transmitted along said shaft to said blade from said sheath;

means directly cooperable between said shaft and said sheath for positively precluding substantial rotational movement of the shaft and sheath in opposite directions relative to one another; and a pair of flats formed on laterally opposite sides of said shaft to form wrench engaging surfaces, a pair of apertures opening through said sheath in registration with and exposing said flats through said sheath for access by a wrench externally of said sheath.

41. Ultrasonic surgical apparatus comprising:

a surgical blade;

a shaft carrying said blade at a distal end thereof and adapted at its proximal end for connection to a power element for generating ultrasonic energy and transmitting the ultrasonic energy along said shaft to said blade;

a sheath extending about and generally radially spaced from said shaft;

means for isolating the ultrasonic energy transmitted along said shaft to said blade from said sheath;

means directly cooperable between said shaft and said sheath for positively precluding substantial rotational movement of the shaft and sheath in opposite directions relative to one another; and the outer diameter of said sheath being no greater than about 5 mm, said sheath being formed of a polymeric material and being connected solely to said shaft, at least one tool engaging surface on said shaft and at least one aperture opening laterally through said sheath exposing said tool engaging surface for access externally of said sheath.

* * * * *

UNITED STATES PATENT AND TRADEMARK OFFICE
CERTIFICATE OF CORRECTION

PATENT NO. : 5,346,502
DATED : September 13, 1994
INVENTOR(S) : Brian K. Estabrook, et al It is certified that error appears in the above-indentified patent and that said Letters Patent is hereby corrected as shown below:

On the title page: Item [54] and Column 1, line 3,

In the title, change "INSTRUMENTS" to --INSTRUMENT --.

Column 11, line 26, before "one-piece" insert --of --.
Column 12, line 55, "at least" should read --at at least--.
Column 13, line 14, after "sheath" insert --at --.
Column 13, line 60, "at least" should read --at at least --.

Signed and Sealed this

Fourth Day of April, 1995

BRUCE LEHMAN

*Attest:*

*Attesting Officer*       *Commissioner of Patents and Trademarks*